(12) United States Patent
Lidgren

(10) Patent No.: US 9,889,233 B2
(45) Date of Patent: Feb. 13, 2018

(54) METHOD OF PRODUCING NATIVE COMPONENTS, SUCH AS GROWTH FACTORS OR EXTRACELLULAR MATRIX PROTEINS, THROUGH CELL CULTURING OF TISSUE SAMPLES FOR TISSUE REPAIR

(71) Applicant: Lars Lidgren, Lund (SE)

(72) Inventor: Lars Lidgren, Lund (SE)

(73) Assignee: ORTHOCELL LIMITED, Murdoc WA (AU)

(*) Notice: Subject to any disclaimer, the term of this patent is extended or adjusted under 35 U.S.C. 154(b) by 0 days.

(21) Appl. No.: 14/940,059

(22) Filed: Nov. 12, 2015

(65) Prior Publication Data
US 2016/0263283 A1 Sep. 15, 2016

Related U.S. Application Data

(62) Division of application No. 12/443,282, filed as application No. PCT/SE2007/000875 on Oct. 2, 2007, now Pat. No. 9,220,803.
(Continued)

(30) Foreign Application Priority Data

Oct. 2, 2006 (SE) ...................... 0602109

(51) Int. Cl.
| | | |
|---|---|---|
| *C12N 5/00* | (2006.01) | |
| *C12N 5/02* | (2006.01) | |
| *A61K 38/00* | (2006.01) | |
| *A61K 38/16* | (2006.01) | |
| *A61K 38/17* | (2006.01) | |
| *A61K 38/18* | (2006.01) | |
| *A61L 27/54* | (2006.01) | |
| *A61K 38/30* | (2006.01) | |
| *A61K 38/39* | (2006.01) | |
| *A61L 15/18* | (2006.01) | |

(Continued)

(52) U.S. Cl.
CPC ............ *A61L 27/54* (2013.01); *A61K 9/0019* (2013.01); *A61K 38/1841* (2013.01); *A61K 38/30* (2013.01); *A61K 38/39* (2013.01); *A61L 15/18* (2013.01); *A61L 27/3604* (2013.01); *A61L 27/3633* (2013.01); *C12N 5/0655* (2013.01); *A61L 2300/252* (2013.01); *A61L 2300/414* (2013.01); *A61L 2300/43* (2013.01); *A61L 2400/06* (2013.01); *A61L 2430/02* (2013.01); *A61L 2430/10* (2013.01); *A61L 2430/20* (2013.01); *A61L 2430/24* (2013.01); *A61L 2430/30* (2013.01); *A61L 2430/32* (2013.01); *A61L 2430/34* (2013.01); *A61L 2430/38* (2013.01)

(58) Field of Classification Search
None
See application file for complete search history.

(56) References Cited

U.S. PATENT DOCUMENTS

| | | |
|---|---|---|
| 5,006,252 A | 4/1991 | Scott et al. |
| 5,635,387 A | 6/1997 | Fei et al. |
| (Continued) | | |

FOREIGN PATENT DOCUMENTS

| | | |
|---|---|---|
| WO | WO 91/02049 | 2/1991 |
| WO | WO 00/57922 | * 10/2000 |
| (Continued) | | |

OTHER PUBLICATIONS

Bilodeau, Katia et al., "Bioreactors for Tissue Engineering: Focus on Mechanical Constraints. A Comparative Review," *Tissue Engineering*, vol. 12, No. 8, Aug. 2006, pp. 2367-2383, XP-002609563.
(Continued)

*Primary Examiner* — Elizabeth C. Kemmerer
(74) *Attorney, Agent, or Firm* — Finnegan, Henderson, Farabow, Garrett & Dunner, LLP

(57) ABSTRACT

A medical composition is disclosed, which is injectable and which comprises a mixture of native components, which are obtainable by culturing one or more cell samples from a human or animal during normal conditions, said native components being included in the group consisting of growth factors, extracellular matrix proteins, and other substances produced by said cell samples during normal conditions, and a pharmaceutically acceptable carrier, as well as a method for producing the native components, a method for producing the medical composition, a method for treating a subject in need of tissue repair by injection of the medical composition, and use of said mixture of native components for the production of said medical composition for tissue repair via injection. A medical composition is disclosed, which is injectable and which comprises a mixture of native components, which are obtainable by culturing one or more cell samples from a human or animal during normal conditions, said native components being included in the group consisting of growth factors, extracellular matrix proteins, and other substances produced by said cell samples during normal conditions, and a pharmaceutically acceptable carrier, as well as a method for producing the native components, a method for producing the medical composition, a method for treating a subject in need of tissue repair by injection of the medical composition, and use of said mixture of native components for the production of said medical composition for tissue repair via injection.

3 Claims, 2 Drawing Sheets

Related U.S. Application Data

(60) Provisional application No. 60/848,399, filed on Oct. 2, 2006.

(51) Int. Cl.
  *A61L 27/36* (2006.01)
  *A61K 9/00* (2006.01)
  *C12N 5/077* (2010.01)

(56) References Cited

U.S. PATENT DOCUMENTS

| | | | |
|---|---|---|---|
| 5,679,636 | A | 10/1997 | Chung et al. |
| 5,989,913 | A | 11/1999 | Anderson et al. |
| 6,096,347 | A | 8/2000 | Geddes et al. |
| 6,284,284 | B1 | 9/2001 | Naughton |
| 2002/0049422 | A1 | 4/2002 | Brewitt |
| 2003/0054544 | A1 | 3/2003 | Gruenberg |
| 2005/0019419 | A1 | 1/2005 | Badylak et al. |
| 2006/0222634 | A1 | 10/2006 | Clarke et al. |

FOREIGN PATENT DOCUMENTS

| | | |
|---|---|---|
| WO | WO 00/69449 | 11/2000 |
| WO | WO 01/14527 A1 | 3/2001 |
| WO | WO 02/24219 A1 | 3/2002 |
| WO | WO 02/067762 A2 | 9/2002 |
| WO | WO 03/046141 A2 | 6/2003 |
| WO | WO 03/046141 A3 | 6/2003 |

OTHER PUBLICATIONS

Brederlau, A. et al., "The Bone Morphogenetic Protein Type Ib Receptor Is a Major Mediator of Glial Differentiation and Cell Survival in Adult Hippocampal Progenitor Cell Culture," *Molecular Biology of the Cell*, vol. 15, Aug. 2004, pp. 3863-3875.

Gazit, Roi et al., "Lethal influenza infection in the absence of the natural killer cell receptor gene Ncr1," *Natue Immunology*, vol. 7, No. 5, May 2006, pp. 517-523.

Grande, D.A. et al., "Evaluation of matrix scaffolds for tissue engineering of articular cartilage grafts," *Journal of Biomedical Materials Research*, vol. 34, (1997), pp. 211-220.

Internationa Search Report from the Swedish Patent Office for International Application No. PCT/SE2007/000875, dated Jan. 30, 2008.

Karim-Abdolrezaee, Soheila et al., "Delayed Transplantation of Adult Neural Precursor Cells Promotes Remyelination and Functional Neurological Recovery after Spinal Cord Injury," *The Journal of Neuroscience*, vol. 26, No. 13, Mar. 29, 2006, pp. 3377-3389.

Supplementary European Search Report dated Dec. 1, 2010 issued in corresponding EP application.

Lu, Yilling et al., "Minced Cartilage Without Cell Culture Serves as an Effective Intraoperative Cell Source for Cartilage Repair," *Journal of Orthopaedic Research*, Jun. 2006, pp. 1261-1270.

\* cited by examiner

//<sub>1</sub>

METHOD OF PRODUCING NATIVE COMPONENTS, SUCH AS GROWTH FACTORS OR EXTRACELLULAR MATRIX PROTEINS, THROUGH CELL CULTURING OF TISSUE SAMPLES FOR TISSUE REPAIR

This is a division of application Ser. No. 12/443,282, filed Dec. 23, 2009, which is a § 371 National Stage of International Application No. PCT/SE2007/000875, filed Oct. 2, 2007, which claims benefit of provisional Application No. 60/848,399 filed Oct. 2, 2006, and claims foreign priority to SE Application No. 0602109-1, filed Oct. 2, 2006, all of which are incorporated by reference.

TECHNICAL FIELD OF THE INVENTION

The present invention relates to a medical composition, to a method for producing a mixture of native components, to a method for producing said medical composition, to a method for treating a subject in need of tissue repair, and to the use of said mixture of native components for the production of said medical composition for tissue repair via injection.

BACKGROUND ART

Replacing or repairing damaged or lost tissue is among the most expensive medical therapies and cost billions of dollars a year all over the world. There is an increasing demand for new methods and materials that can be applied in tissue engineering.

The experience of transplanting multiplied stem cells or specific donor stem cells into the human body, e.g. in joints, heart, brain and endocrine organs, has not been successful in showing significant long term survival of the transplanted cells. In a few studies, however, some impact on vascular ingrowth and repair with cell recruitment and minor clinical improvement has been reported.

The most obvious reason for the reported short term effect of transplanted stem cells on local repair (Gazit et al. 2006) is in our opinion that the transplanted cells during their short survival time act as a local cell factory producing a cascade of growth factors and extracellular matrix proteins capable of recruiting progenitor stem cells. Recent studies using colony-stimulating factors to enhance local tissue generation recruiting existing local or circulating stem cells strengthen this hypothesis. It has been demonstrated that the human brain contains cells with stem cell-like properties and an ability to generate new neurons from generator stem cells (Brederlau et al 2004). It has also recently been shown that the combination of transplanting neuroprecursor cells together with single growth factors in injured rat spinal cord in an acute phase will slightly improve the nerve function. The same effect was not seen if the transplantation was carried out after 8 weeks (Karima et al. 2006).

Bio-engineered tissue has been successfully used for replacement purposes in a limited number of clinical applications for example in the treatment of bone defects, diabetic ulcers and for tendon ruptures. The most successful approach has been to select different cell types that exhibit the function and characteristics of the tissue of interest. The best long term results have been reported in the knee for isolated chondral defects using autografts, i.e. chondrocytes cultured in a bioreactor on a scaffold using, for example, a 3-dimensional matrix, a collagen fleece or hyaluronan. However, mincing cartilage and distributing it on a similar matrix in a one-stage procedure without prior culturing gives as good results as with autologous chondrocyte implantation. In both cases a hyaline-like cartilage will be the result. The implant will often integrate poorly with neighbouring cartilage. This almost always gives a scar tissue leaving a cleft, in the area between healthy cartilage and the transplant (Yiling et al 2006).

In WO2002/067762 A2 a muscle polymer construct for bone tissue engineering is described, wherein a bone grafting material comprising a polymer scaffold loaded with bone morphogenetic proteins and populated with muscle cells is prepared to synthesize bone tissue.

In US20050019419 a tissue graft composition comprising liver basement membrane and a method of preparation of this tissue graft composition are described. The graft composition can be implanted to replace or induce the repair of damaged or diseased tissues.

U.S. Pat. No. 6,096,347 describes the use of submucosal tissue of a warm-blooded vertebrate to manufacture a tissue graft composition that induces the formation of endogenous cardiac tissues in vivo upon contact of the cardiac tissues with the manufactured composition.

WO 01/14527 refers to a conditioned medium composition containing skin agents produced from cultured cells of skin and a carrier agent for topical application on the skin.

US 2002/0049422 A1 discloses a topical composition comprising different growth factors.

WO 02/24219 refers to an isolated protein complex comprising a growth factor binding protein, vitronectin and a growth factor, as well as a surgical implant and a skin regeneration medicament comprising said complex.

In view of the prior art there still remains a need to improve the replacing and repairing of damaged or lost tissue within the body of human and animal subjects. The applications of repairing and replacing damaged or lost tissue are extensive and the conditions to be treated are many.

As will be apparent from the following, the present invention is directed to solving such needs.

SUMMARY OF THE INVENTION

The present invention relates, in one aspect, to a medical composition which is injectable and which comprises a mixture of native components, which are obtainable by culturing one or more cell samples from a human or animal during normal conditions, said native components being included in the group consisting of growth factors, extracellular matrix proteins, and other substances produced by said cell samples during normal conditions, and a pharmaceutically acceptable carrier.

The present invention relates in a further aspect to a method for producing a mixture of native components comprising the steps of:
  adding one or several different cell samples of human or animal origin to a bioreactor containing a nutrient medium, wherein a culturing medium is obtained;
  cell culturing during normal conditions;
  drawing off at least once the culturing medium including the native components produced during the cell culturing;
  separating the native components from the culturing medium thereby obtaining a mixture of native components.

The present invention relates in still a further aspect to a method for producing the medical composition, wherein a carrier is added to the mixture of native components produced, before or after an optional freeze-drying step.

The present invention relates in another aspect to a method for treating a human or animal subject in need of tissue repair by injection of said medical composition.

The present invention relates in still another aspect to use of said mixture of native components for the production of said medical composition for tissue repair via injection.

DESCRIPTION OF PREFERRED EMBODIMENTS OF THE INVENTION

Figure 1:
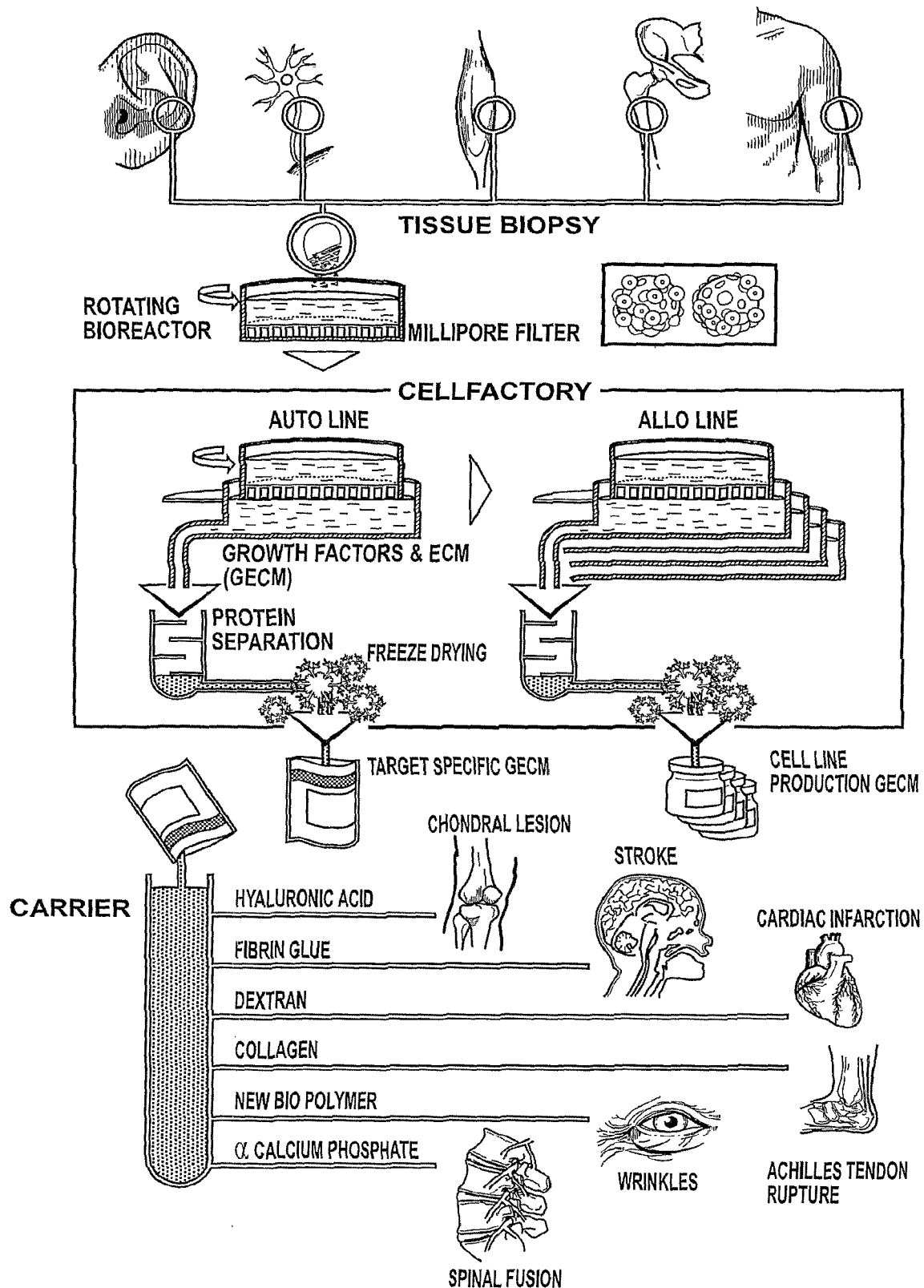
FIG. 1 depicts one embodiment of the method according to the invention, wherein cells are taken from a certain kind of tissue and thereafter are cultured in one or more bioreactors. The native components produced, such as growth factors and an extracellular matrix proteins (GECM), are then combined with a chemically and mechanically optimized carrier, wherein a medical composition is formed. This is then injected into the host tissue where the cells are recruited and proliferation and differentiation are enhanced.

In one embodiment, the method according to the invention further comprises freeze-drying of the separated native components such as GECM. Any conventional freeze-drying method known to a person skilled in the art may be used.

According to the present invention, each cell sample is or originates from a tissue biopsy from a human or animal subject. Examples of animal subjects from which the tissue biopsy can be taken are preferably, but not limited to, pigs, cows, and goat. The tissue biopsy is preferably taken from, but is not limited to, one or more of the following tissues: muscle, fat, cartilage, skin, nerves, liver, bone, and/or teeth.

In the present context, the wording "tissue biopsy" is meant to be a biopsy taken from any tissue in the body directly by removing the desired sample and adding the sample directly to the bioreactor. Preferably, the tissue biopsy may be minced, enzymatically degraded, treated or enriched before adding it to the bioreactor.

In the present context, the wording "cell sample of human or animal origin" is meant to mean a cell sample taken from a human or animal at any developmental stage, i.e. any stage from fertilization and onwards, e.g. a cell sample taken from the embryonic stage or before the embryonic stage or at any other developmental stage. The cells to be cultured could be target-specific for, for example, a joint, elastic cartilage in the ear, nerves, hip abductor muscles, tendons from fascia lata, skin from the upper arm, and mesenchymal cells from the iliac crest etc.

In the present context, the wording "one or several different cell samples" means that one specific cell sample from a certain tissue may be used in the subsequent cell culturing step. More than one cell sample may also be used, i.e. two or more cell samples from different tissues, for instance one cell sample from muscle and one cell sample from cartilage etc, but only in specific situations or when the different tissues have additional stimulatory effects.

In the present context, the wording "bioreactor" is meant to be a conventional bioreactor available for culturing of cells. A person skilled in the art may easily select a known reactor to be used in the method of the invention. In one embodiment, use is made of a bioreactor with two or more interconnected chambers separated by a millipore filter which allows for the native components produced, such as growth factors and extracellular matrix proteins (ECM), to diffuse into the second chamber or third chamber and so on. At predetermined intervals the culturing medium is drawn off and the native components separated and freeze-dried under sterile conditions.

The native components produced may be sterilized by use of any one of several sterilization techniques, e.g. by $\beta$ or $\gamma$ radiation at least 1.2 MRad; by sterile filtration, wherein the whole process including the freeze-drying and packaging is performed in a sterile bench; or by use of gassing with ethylene oxide (ETO). During the gassing operation the package, e.g. a bag, in which the treated medical product is placed for storage after freeze-drying, has to be degassed during several weeks, normally about 4-6 weeks, wherein the ethylene oxide inside the package slowly leaks out from the walls of the package.

In the present context, the wording "culturing medium" should be distinguished from "nutrient medium". The nutrient medium is the fresh medium with all the necessary nutrients required for growth of the cells, before the cells have been added. Once the cells have been added to the nutrient medium the medium will be regarded as a culturing medium with the cells included as well as the native components produced during cell culturing. When drawing off the culturing medium including the native components the cells are usually not present in the culturing medium as they have already been separated from the culturing medium in the bioreactor with the two interconnected chambers. However, it is possible that parts of the cells and a small number of cells are included in the culturing medium after filtration. Alternatively, in another embodiment, the cells are included in the culturing medium when drawn off from the bioreactor and are thereafter separated from the culturing medium by any conventional means.

In the present context, the wording "nutrient medium" means a nutrient medium as used in its conventional context, i.e. a medium such as DMEM or specific growth media suitable for different cells and cell lines, which allows for the growth of cells and for the production of the native components. The nutrient medium should provide certain conditions, such as hormones or growth factors that usually occur in vivo. The choice of nutrient medium is dependent on the desired direction of cell growth and the cells used. Substances that may be present in the nutrient medium are growth factors, nutrients such as glucose or other sugars as needed. Other substances that may be included in the nutrient medium are, for instance, antibiotics.

In the present context, the word "normal conditions" is used to define the environment in which the cells proliferate and stay viable in the same or essentially the same manner as in their natural environment such as in the human or animal body. A person skilled in the art is familiar with what is meant by normal conditions and is able to arrange for this during culturing.

In another embodiment, the cell sample is a specific cell line. The cell line can be commercially available. Any known cell line that is commercially available can be used according to the invention and a person skilled in the art can easily select any cell line suitable for producing the native components as required by the ultimate application. The advantage of using a commercially available cell line is that the many different native components of different origin can be produced and stored. When a patient needs immediate tissue replacement or reparation due to damaged or lost tissue, such as cardiac infarction or cerebral haemorrhage, the stored native components produced by the commercially available cell lines may be used directly by injecting the medical composition comprising the native components with the desired carrier, if needed. In some instances, immediate access to the native components and the carrier is required within the first few days or weeks following an acute emergency or injury. There are today commercial cell-lines that could be used for repetitive drawing off of the native components, thus making them available instantly in emergency situations. Specific markers, such as TGF-beta and IGF-1 and extracellular matrix proteins, could be used as marker proteins to establish the concentration. In these cases, the native components are of an allograft type, i.e. not the patients own native components.

In the present context, the phrase "native components" is meant to comprise all growth factors, all extracellular matrix proteins (ECM), and all further substances that are produced by the cells in their natural environment including native polymers and other proteins. In the present context, exactly the same components are produced in a bioreactor as in the natural environment of the specific cell. Depending on the tissues from which the cells to culture are taken, there are probably hundreds of different proteins, biopolymers, and other substances and molecules that are produced. Extracellular matrix proteins are for instance, but are not limited to, fibronectin, vitronectin, chondroadherin and aggrecans.

In one embodiment, it is of interest to produce and isolate only growth factors and extracellular matrix proteins (ECM). The combination of these is also called GECM (Growth factors and Extra Cellular Matrix proteins). These are the most important of the native components as they provide an optimal balance between downregulation and upregulation of the tissue regeneration process in which they are to be involved. However, in practice, all of the molecules defined by the expression "native components" are automatically present in the mixture or cocktail obtained and are effective for the subsequent regeneration process within the body, although highly satisfactory results also are obtained with only the GECM mixture.

A further embodiment of the invention is to provide a carrier, which retain native components such as GECM and slowly releases them during a prolonged period of time (i.e. days, weeks or months) and which makes the medical composition including the native components and the carrier injectable into the human and animal body. As have been stated before, the carrier is selected according to the ultimate application, i.e. the organ or place in the body where the carrier is to be injected.

In the present context, the term "native" means that the native components, of which several are proteineous, are in their non-denatured state. Any chemical modification of the component is thus allowed as long as the biological activity is retained.

Examples of proteineous components are a parathyroid hormone, a prostaglandin (e.g. $PGE_2$), an osteoprotegrin (OPG), Indian hedgehog activator, an NF-kappa B ligand (RANKL), a sex steroid, and a cytokine.

A growth factor is, in the present context, a general term for specific peptides or proteins, which are released by certain cells and bind to specific cell membrane receptor sites to influence cells to divide. For example, chondrocytes produce a number of growth factors, including, for instance, transforming growth factor (TGF-β3), bone morphogenic protein (BMP-2), PTHrP, osteoprotegrin (OPG), Indian hedgehog activator, RANKL, basic fibroblast growth factor (bFGF) and insulin-like growth factor (IgF). The platelet-derived growth factor (PDGF) is a glycoprotein that stimulates cell proliferation and chemotaxis in cartilage, bone, and many other cell types after being produced by mesenchymal cells. Likewise, the basic fibroblast growth factor (bFGF) is produced locally in bone during the initial phase of fracturing healing and is known to stimulate cartilage and bone-forming cells.

The super family of transforming growth factors (TGFs) is the most extensively studied growth factor in the field of bone biology. It comprises an entire family of substances that includes the bone morphogenetic proteins (BMPs). These are important cell-cell signalling substances, which induce cartilage and bone formation as well as promote the differentiation of osteogenic precursor cells into osteoblasts. It should be noted that pure forms of BMPs, some produced by genetic engineering, are non-immunogenic and non-species-specific.

The growth factor can also be a fibroblast growth factor (FGF) or a vascular endothelial growth factor.

A mixture of autologous growth factors, which is derived from the buffy coat of cells collected during surgery, is produced by Interpore Cross International Inc., Irvine, USA. These leukocytes are said to be especially rich in TGF-β and PDGF. A cocktail of growth factors from a bovine-derived bone morphogenetic protein extract is also produced by NeOsteo, Intermedics Orthopaedics, Denver, USA.

The amounts of different components in the medical composition depends on the cell and tissue origin of the native components produced as well as on the final application intended, i.e. the kind of tissue or organ to be repaired.

Normally, the proportion between the native components and the carrier in the final medical composition is about 1:10 on weight part basis, but this proportion may vary somewhat.

Preferably, cells of human origin are used as "factories" for producing the native components. A suitable mixture or cocktail of growth factors, obtained from cultured chondrocytes, can be up to for instance 100 kDa in size or more, such as between about 70 kDa and 10 kDa, preferably between about 60 kDa and 20 kDa, more preferably between 50 kDa and 30 kDa. The size of the components is naturally not limited to the above sizes since these are only exemplifying.

The wordings "mixture of native components" and "cocktail of native components" used herein are intended to mean a set of all or a part of the native components as defined above produced from a certain cell, cell line or tissue, i.e. all of the components produced in their natural environment. If desired, some of said native components could be removed from the medium after culturing with a view to maintaining only the most important native component for the subsequent application, e.g. growth factors and extracellular matrix proteins (GECM). As stated above, native components originating from different cells, cell lines, and tissues may be present in the same mixture or cocktail of native components. Such mixtures are also intended to fall within the scope of the expression "mixture or cocktail of native components".

In one embodiment of the invention, the cell culturing is carried out under rotating conditions. The rotation causes a better nutritional flow, which makes the cells proliferate and produce GECM better. The rotation can be implemented by any conventional rotating means used in conventional cell culturing. In certain embodiments, the rotation may naturally be excluded. It is further suitable, but not necessary, that a three-dimensional matrix is present under the cell culturing in order to increase the production of the native components. It is beneficial if the matrix is spherical, for instance starch beads, which have an interconnected pore system for dynamic nutritional flow. The matrix can be chosen from, but is not limited to, beads, starch beads, polymer beads, and beads of alginate, collagen, hyaluronic acid, and chitosan. Any known matrices such as three-dimensional matrices that are suitable for use in cell culturing may naturally be used in accordance with the invention. A person skilled in the art realizes what kind of matrices can be used for beneficial growth.

In one embodiment of the invention, the drawing off of the culturing medium including native components takes place continuously and the drawn-off culturing medium is replaced with new nutrient medium. In one embodiment, two interconnected chambers separated by a millipore filter can be used for cell culturing, which allows for the native components, e.g. growth factors and ECM protein molecules, to diffuse into the second chamber. At pre-determined intervals the culture media could be drawn off and the native components separated and freeze-dried under sterile conditions, see FIG. 1. The cell culturing is carried out during for at least 7 weeks, preferably at least 5 weeks, more preferably at least 3 weeks, and most preferably at least 1 week, or less, e.g. 1, 2, 3, 4, 5, or 6 days, before the drawing-off step is performed.

In one embodiment of the invention, the native components produced are separated from the culturing medium by their size or weight or by affinity, e.g. by centrifugation or are separated in a column.

After separation the separated single native components may be combined in a mixture or cocktail before freeze-drying, as described above. Alternatively, each of the separated native components is further enriched before freeze-drying. After freeze-drying, the freeze-dried mixture or cocktail may be stored in a bag until use. As stated above, it is also possible to enrich any of the separated components, combine them in a cocktail and then freeze-dry the same. Thus, it is possible to obtain one or more native components from biopsies of different origin (i.e. from different tissues) and then combine the obtained components after culturing in a novel cocktail and then optionally freeze-dry the cocktail.

According to the present invention, a carrier is added to the separated native components before or after freeze-drying. In a further embodiment, freeze-drying is not necessary, e.g. in acute situations in which an injection is to be made immediately. Thus, it depends on the ultimate application whether a carrier is to be included or not before freeze-drying. The carrier has to be injectable into the human and animal body when mixed with the native components, and is chosen in view of the ultimate application, otherwise the body of the human or animal patient could have difficulties accepting the native component carrier product. The term "injectable" used herein means that the medical composition, i.e. the mixture of native components and carrier, and any further pharmaceutically acceptable auxiliary components, e.g. antibiotics and rheology enhancing components needed, to be introduced into the human or animal body can be injected into the body through a needle or tube having an inner diameter of 0.2-6 mm, preferably 0.4-2 mm. This means that such parameters as viscosity and carrier material size of the medical composition according to the present invention must be optimized for fulfilling this purpose, which is familiar to a person skilled in the art. Certain carriers are only suitable for certain applications, which is obvious to a person skilled in the art. The carrier must of course be acceptable by the human and animal body and is chosen from the group consisting of natural or synthetic polymers, and ceramic materials which are well-known in the art to be injectable. The carrier may be chosen from, but is not limited to, hyaluronic acid, fibrin glue, chitosan, dextran, collagen, alginate, and biopolymers of different materials having different modules of elasticity. The biopolymer of different materials having different modules of elasticity may be prepared by welding/binding together two different materials, for example a metal and a plastic, or a natural and synthetic polymeric material. Other materials that can be used in this biopolymer are, for instance, any organic and inorganic materials. It is also possible that the biopolymer is a biopolymer with an elasticity gradient within the same material.

Figure 2:
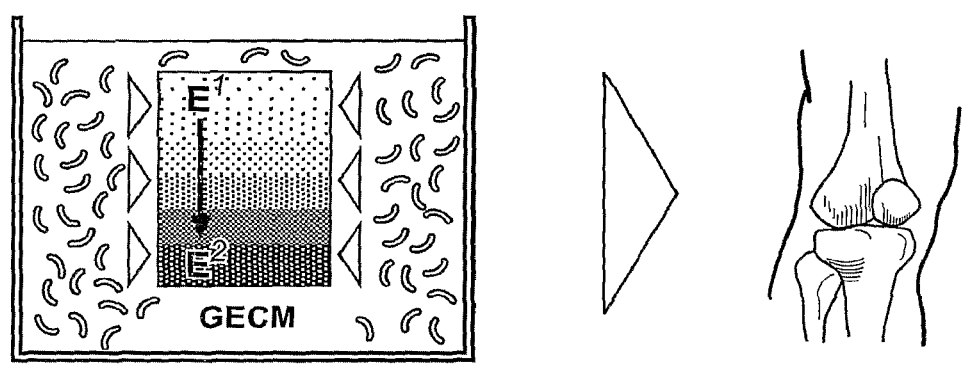
FIG. 2 depicts a carrier with different modules of elasticity being soaked or preloaded with the native components, such as GECM produced according to the invention.

In one embodiment of the invention the development of modifications of natural polymers, synthetic polymers and/or ceramic materials with different elastic and viscoelastic properties will be prepared, see FIG. 2. The carriers could be soaked or pre-loaded or fabricated with prepared native components such as GECM and/or combined with other factors such as biphosphonates or antibiotics and eventually be combined with the systemic application of colony stimulating factors or drugs to enhance recruitment of circulating progenitor cells and cell binding proteins.

In one embodiment, the mixture of native components may be injected directly, i.e. without having been mixed with any carrier, into or close to a carrier, e.g. an implant, which is already present in the body at the site at which the tissue regeneration is to take place.

The native component(s) produced according to the method of the invention, when ultimately administered to the subject, are of an autograft or allograft character or both. The advantages of autografts to a patient are realized since these are the patients' own native components that are used, whereby for instance rejection is avoided. Other problems that are avoided are infections due to different viruses that are transferred to the host, even if the transferred implant is sterilized. Thus, virus infections such as HIV and infections caused by prions or any other species can be avoided when the implant is of an autograft type.

The tissue repair could, for instance, take place in, but is not limited thereto, joints, vascular parts, muscles, tendons, the spinal cord, nerves, bone tissue, fat tissue, heart, brain, and endocrine organs. For instance, the specific native components prepared could be injected to biological carriers like hyaluronic acid to be used for joint injuries, fibrin glue for Achilles tendon injuries, bi-phasic α-tricalcium phosphate (injectable bone substitute) for vertebral fractures and spinal fusion, dextran for spinal cord injuries etc, provided that the carrier has been implanted in advance at the place of the tissue repair process. Other areas where the native components could be used are stroke, Parkinson's disease and Alzheimer's disease using available proven biological carriers. It is also possible to use the inventive native components with a carrier as an implant for implantation to a patient who has had an organ, preferably an endocrine organ, or part of an organ removed, and in order to provide a faster re-growth of the organ tissue an implant (carrier including native components) as provided herein is implanted to the patient.

In accordance with the present invention, a method for treating diseases such as, but not limited to, stroke, myocardial infarction, Parkinson's disease, Alzheimer's disease, cerebral haemorrhage, bone diseases, muscle diseases, peripheral nerve injuries and tendon disease, has been provided.

In a further embodiment a carrier, e.g. in the form of a polymer, may be added to the reactor containing the cells to be cultured. The native components produced and brought to pass the filter(s) in the reactor may then be recirculated back to the part of the reactor containing the carrier and the cells to be cultured, wherein the native components are bound to the carrier. Such a carrier including the native components, e.g. growth factors and ECM proteins, may then be implanted directly into a tissue repair place in the human or animal body.

In still another embodiment, a carrier may be placed in a separate container through which native components produced are brought to pass, wherein said native components are bound to said carrier, which then may be implanted directly at a tissue repair site in the human or animal body.

EXAMPLES

Preliminary studies (see details below) have been performed with chondrocytes as cell samples taken from six human knees at surgery, cultured in a bio-reactor with the culture media obtained and the GECM produced separated from the cells at 3 weeks. Three different concentrations of the GECM cocktail were incorporated into an injectable material and implanted into rat abdominal muscle. A biphasic ceramic bone substitute was used as a carrier, and measurements with TGF-beta and IGF-1 as markers showed a clear dose response curve. Vascular ingrowth and new bone could be demonstrated in the synthetic material in a muscle. This is only possible by the recruitment of circulating or local progenitor cell-stem cells that differentiated muscle cells into bone.

In another study (see details below) we have tested whether one type of ECM, chondroadherin, a non-collagenous cartilage protein with cell binding properties could be used in the same ceramic bi-phasic bone substitute to induce bone.

It has been concluded earlier that chondroadherin may play a role in maintaining bone cells on collagen matrices. We used an α-tricalciumphosphate and calcium sulphate bone substitute in an animal rabbit model with a well described bone harvest chamber. The pharmacokinetics was studied showing a significant release of chondroadherin and increase over the first two weeks. However, it was not possible to show any significant increase in new bone whether as apposition or growing into the material. Looking at the specific activity counting for instance the number of osteoclasts on the material again, showed no difference to the plain bone substitute.

One could speculate that a different carrier or ECM would make a difference. However, it is more likely that either the concentration of chondroadherin was too low to show any effect or that a combination of extracellular matrix proteins and growth factors would be necessary to significantly increase the recruitment of circulating or local progenitor cells to transform and induce bone.

Detailed Description of Preliminary Experiment 1

Growth Factor Cocktail

An autologous growth factor chondrocyte cocktail (AG-FCC) was produced from ex vivo cultured, human cartilage cells. During arthroscopic examination the surgeon took a biopsy from the non-weight-bearing area of the proximal part of the medial or lateral condyle. The cartilage chip was 8 to 10 mm long and extending down to the subchondral bone plat. The biopsy contained roughly 200-300 mg of cartilage. The biopsy material was immediately placed in the nutrient medium and forwarded to a cell laboratory and placed in a special nutrient solution (DMEM F-12).

Production of Growth Factor Cocktail

The cell nutrient medium consisted of DMEM F-12. The cells were cultured in a medium for about 2 weeks, whereafter the culturing medium was collected and saved as a 100×-concentrated portion. TGF-β and IGF-I served as marker proteins to establish the concentration of the growth factor cocktail. The amount of TGF-β in the highest concentration of the medium was about 50-300 ng/ml and that of IGF-I was about 100-300 ng/ml. The cocktails were produced from 7 patients.

Mixture of Bone Substitute

The α-TCP with 20% CaS was mixed with the respective cocktails, the high concentrated (100 times) cocktail was diluted 10 times and 100 times with 1% BSA-PBS. With the concentrations, the materials were divided by IBS-GF1 (high concentration), IBS-GF3 (low concentration). After mixing the material was injected into a mould (5 mm in diameter×4 mm thick) and left until set (12 h). The set pellets made from the injectable material were implanted in rat's muscles.

Animal Experiments 64 female Sprague-Dawley rats with body weights of 200-230 g were used for the experiment. The operation was performed under anaesthesia with chloral hydrate (300 mg/kg, B.W. intraperitoneally). The prepared specimens made from the injectable material were implanted in abdominal muscle pouches of rats. 8 rats in each group were killed at each of the following time intervals; 3, 6, 12 and 24 weeks.

Specimen Preparation and Evaluation

The bone substitutes with surrounding muscles were harvested. The sample specimens with tissue and materials were fixed in 4% formalin in buffer, decalcified and embedded in paraffin. They were cut into 5μ sections and stained with H&E staining. The histological analysis was done by observing osteoblasts, mineralization and trabecular bone in and around the materials. The size of new bone formation area was counted by using a microscope with a computer imaging system (Kontron Bildanalyse, Germany). The score of bone induction was done by a score standard under microscope.

Single ECM Experiment, Chondroadherin

Biomaterial as carrier and chondroadherin as native component were combined with the aid of a 2.5% aqueous di-sodium hydrogen phosphate solution forming a paste. The paste was then distributed into moulds to form small cylindrical pellets each of 1 mm diameter and height. During in vitro tests, once dried, pellets were immersed in 100 microliters of phosphate buffered saline solution and left to dissolve at room temperature. At periodic intervals ranging from 15 minutes to 2 weeks, the bathing solution was removed, centrifuged, and run through a UV-Vis spectrophotometer (at 280 nm) to record absorbance readings. Each solution was then replaced back into the appropriate vial and the dissolution process allowed to continue. It was hoped that absorbance readings would reflect the proportion and subsequent rate of release of chondroadherin into the surrounding solution as pellets gradually dissolved.

During tests carried out in vivo, a single pellet made from the injectable material was implanted bi-laterally into the proximal tibiae of 6 rabbits with the aid of a bone chamber. One side contained a pellet with incorporated chondroadherin while the other served as a control. Bone in-growth was then assessed via histological analysis following harvest at intervals of 2 and 3 weeks. No bone ingrowth was observed.

The invention claimed is:

1. A method for treatment of a human or animal subject in need of tissue repair comprising preparing a medical composition and injecting the medical composition into the human or animal subject, wherein the medical composition comprises a mixture of native components included in the group consisting of growth factors, extracellular matrix proteins and other substances produced by cell samples during normal conditions, wherein the steps of preparing the medical composition comprise:

adding one or several different cell samples of human or animal origin to a bioreactor containing a nutrient medium, wherein a culturing medium is obtained;

cell culturing during normal conditions, wherein the cell culturing is carried out under rotating condition;

drawing off at least once the culturing medium including native components produced during the cell culturing;

separating the native components from the culturing medium thereby obtaining a mixture of native components, wherein the drawing off takes place continuously and the drawn-off culturing medium is replaced with new nutrient medium, said bioreactor having two or more interconnected chambers separated by a Millipore filter which allows for the culturing medium containing native components produced to diffuse into a second chamber or third chamber and so on and for separation of the cells from the culturing medium containing native components in the bioreactor, and injecting the medical composition into the human or animal subject wherein said tissue repair takes place in joints, muscle, tendon, fat tissue, or heart of the human or animal subject.

2. The method according to claim 1, wherein the medical composition is of an autograft or allograft type or both.

3. The method according to claim 1 for treating a subject for myocardial infarction, muscle disease or tendon disease.

* * * * *